United States Patent [19]

Takeshita

[11] 3,963,792

[45] June 15, 1976

[54] PROCESS FOR PRODUCTION OF CYCLIC POLYENES

[75] Inventor: Yasuhiro Takeshita, Chiba, Japan

[73] Assignee: Idemitsu Kosan Co., Ltd., Tokyo, Japan

[22] Filed: Aug. 26, 1974

[21] Appl. No.: 500,700

[30] Foreign Application Priority Data

Aug. 30, 1973 Japan.................... 48-96626

[52] U.S. Cl. ............... 260/666 A; 260/586 M; 260/23 R; 252/429 C; 252/9

[51] Int. Cl.² ............... C07C 3/10; C07C 13/00

[58] Field of Search ................ 260/666 A

[56] References Cited

UNITED STATES PATENTS

| | | | |
|---|---|---|---|
| 2,969,408 | 1/1961 | Nowlin et al. ........... | 260/666 A |
| 3,622,644 | 11/1971 | Kubicek et al. ........... | 260/666 A |
| 3,853,748 | 12/1974 | Tabler ........... | 260/666 A |

OTHER PUBLICATIONS

Truffault et al., comptes rendus 231 1068–1070 (1950).

*Primary Examiner*—D. Horwitz
*Attorney, Agent, or Firm*—Flynn & Frishauf

[57] ABSTRACT

Process for producing cyclic polyenes having the general formula

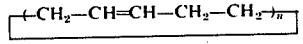

wherein $n$ is at least 2 by contacting cyclopentene with a complex catalyst of (i) trialkyl aluminum, (ii) wolfram hexahalides and (iii) allyl halides or methallyl halides. The invention also provides novel 15 carbon cyclic polyenes.

8 Claims, 1 Drawing Figure

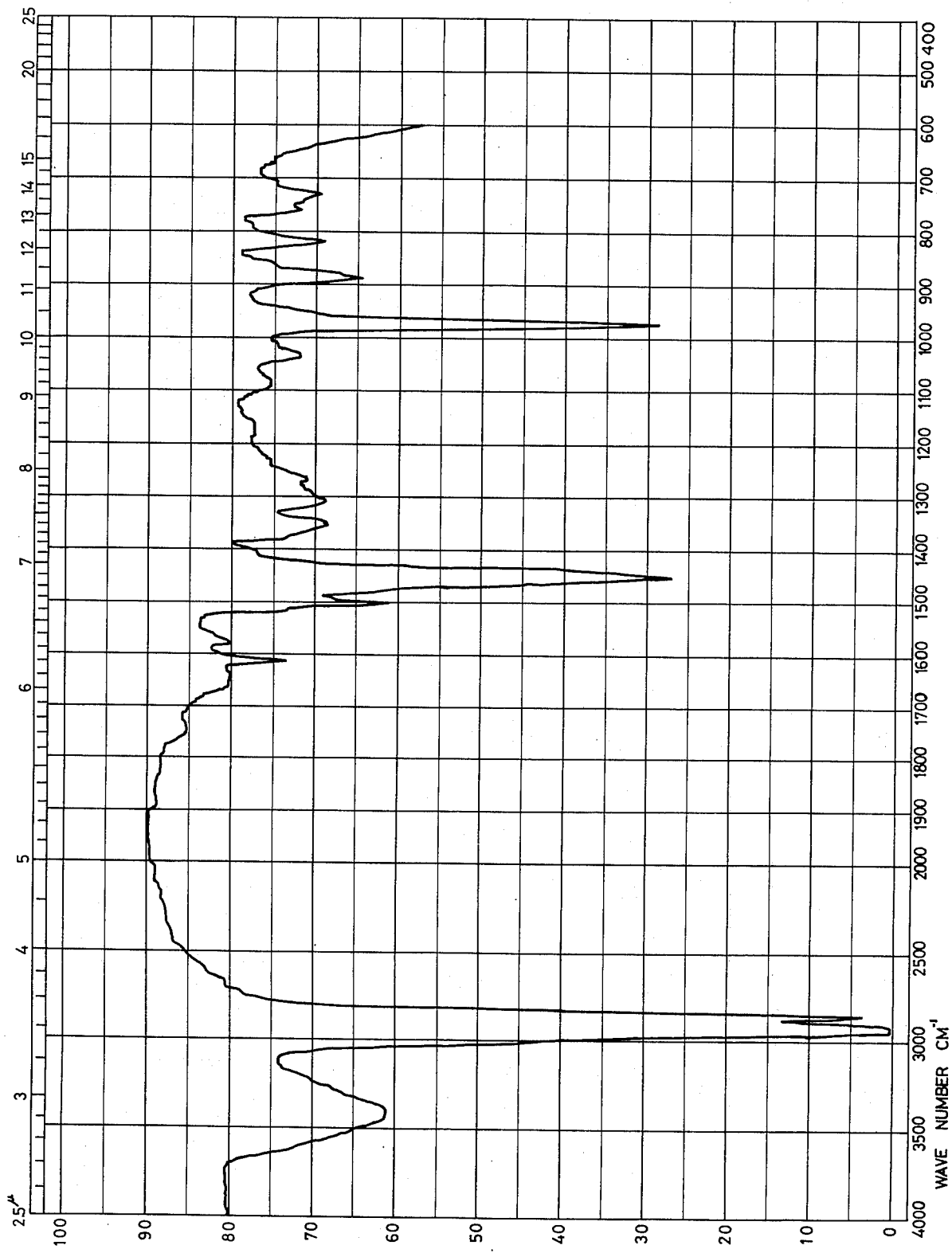

PROCESS FOR PRODUCTION OF CYCLIC POLYENES

BACKGROUND OF THE INVENTION

1. Field of the invention

The present invention relates to a new process for the production of cyclic polyenes and more particularly it relates to a process for producing cyclic polyenes having a general formula of $$[-CH_2-CH=CH-CH_2-CH_2-]_n$$

wherein $n$ is at least 2.

2. Description of the prior art

Heretofore, various processes have been disclosed for the synthesis of cyclic polyenes by dimerization, trimerization, or oligomerization of acetylene, olefins, diolefins and the like. However, feasible processes for synthesis of cyclic polyenes by polymerization of cyclopentene to produce dimers, trimers, tetramers and other relatively short chain polymers are not known yet.

It has been known that the use of the catalyst combination of trialkyl aluminum and wolfram hexahalide results in ring-opening polymerization and the formation of high molecular weight polyenes.

SUMMARY OF THE INVENTION

The present invention provides a process for producing cyclic polyenes of the general formula $$[-CH_2-CH=CH-CH_2-CH_2-]_n$$

wherein $n$ is at least 2, by contacting cyclopentene with complex catalyst consisting essentially of trialkyl aluminum, wolfram hexahalide, and allyl halide or methallyl halide.

BRIEF DESCRIPTION OF THE DRAWING

FIG. 1 illustrates IR absorption spectrum (KBr method) of component (2) of Example 1.

DETAILED DESCRIPTION OF THE INVENTION

The catalyst combination of the present invention, sometimes referred to as a "complex catalyst", consists essentially of the said trialkyl aluminum, wolfram (tungsten) hexahalide, and the allyl halide or methallyl halide. The cyclic polyenes are only obtained when the catalyst combination contains the said allyl halide or methallyl halide. In the process of the present invention, dimers, trimers, and tetramers of cyclopentene are formed selectively.

The trialkyl aluminum component of the catalyst combination preferably contains as the alkyl group a $C_1$–$C_6$ alkyl group, such as methyl, ethyl, propyl, butyl and hexyl.

The halogen forming the said wolfram hexahalide and allyl halide or methallyl halide are usually chlorine, bromine or iodine.

In the catalyst of the process of the present invention, the molar ratio of trialkyl aluminum to wolfram hexahalide is preferably 4–15:1, and the molar ratio of allyl halide or meta-allyl halide to wolfram hexahalide is preferably 40–120:1. The amount of wolfram hexahalide is not specified and so-called catalytic amounts are sufficient for the synthesis. Preferably, wolfram hexahalide is employed in the range of from 0.0001 to 0.1 moles per 1 mole of cyclopentene.

The reaction temperature is generally from −20° to 100°C, preferably from 0° to 60°C.

The invention is further described by the following specific examples which are merely intended to be illustrative and not limiting. Unless otherwise stated, percent (%) in the examples indicates weight percentage.

COMPARATIVE EXAMPLE 1

Toluene (38 ml) and cyclopentene (8.2 g) were poured into a 100 ml two-necked flask under a stream of argon. Wolfram hexahalide (0.10 mmol) and triethyl aluminum (0.40 mmol) were added as the catalyst and the reaction proceeded for 4 hours at 25°C. After the completion of the reaction, polymers were precipitated in methanol and the polymers were dried in vacuo giving 0.41 g of highly polymerized polymer having strong rubberlike elastomers.

EXAMPLE 1

Toluene (100 ml) and cyclopentene (30 ml) were poured into a 300 ml two-necked flask under a stream of argon and then maintained at 25°C. Subsequently, allyl chloride (10 mmol) and 5.0 ml of wolfram hexachloride solution (0.052 mmol/ml of benzene) were added and 2.0 ml of triethyl aluminum solution (1.015 mmol/ml of n-heptane) was added as the catalyst. The reaction was immediately and spontaneously initiated, and was continued for 3.5 hours. After the completion of the reaction, the catalysts were degraded by adding small amounts of methanol. The reaction mixture was distilled at ambient pressure to remove solvents and then was distilled under reduced pressure to yield the following components:

| | | |
|---|---|---|
| (1) | b.p 82 – 83°C/30 mmHg | small amounts |
| (2) | b.p 86 – 89°C/4 mmHg | 52.0% |
| (3) | b.p 153 – 154/2.5 mmHg | 40.0% |
| (4) | residues with high boiling point | 7.9% |

Conversion yield of cyclopentene was 84%.

(1), (2) and (3) were found to be the cyclic dimer, trimer and tetramer of cyclopentene, respectively, by study of the IR absorption spectra, NMR spectra and determination of molecular weight (V.P.O. method) on the said three distillates (1), (2) and (3).

| | Molecular weight | |
|---|---|---|
| | obs. | calc. |
| Component (2) | 196 | 204 |
| Component (3) | 264 | 272 |

EXAMPLE 2

The reaction was conducted in the same manner as described in Example 1 except that the reaction temperature was kept at 40°C. The conversion yield of cyclopentene was 89%. The amounts of components (1), (2), (3) and (4) which were the same as described in Example 1, were a small amount, 53.4%, 31.3% and 15.2%, respectively.

EXAMPLE 3

The reaction was conducted in the same manner as described in Example 1 except that the reaction temperature was maintained at 60°C. The conversion yield of cyclopentene was 91.5%. The amounts of components (1), (2), (3) and (4) were a small amount, 55.0%, 20.2%, and 24.6%, respectively.

EXAMPLE 4

The reaction was conducted in the same manner as described in Example 1 except that the amount of allyl chloride was 30 mmol. The conversion yield of cyclopentene was 87.2%. The amounts of components (1), (2), (3) and (4) were a small amount, 51.9%, 33.0%, and 15.0%, respectively.

EXAMPLE 5

The reaction was carried out in the same manner as described in Example 1 except that tri-isobutyl aluminum was used in place of the triethyl aluminum and the reaction temperature was maintained at 40°C. The conversion yield of cyclopentene was 56.9%. The amounts of components (1), (2), (3) and (4) were a small amount, 50.0%, 14.3%, and 35.7%, respectively.

EXAMPLE 6

The reaction was carried out in the same manner as described in Example 1 except that allyl bromide was used as the allyl halide component, and the reaction temperature was set at 40°C. The conversion yield of cyclopentene was 26.8%. The amounts of components (1), (2), (3) and (4) were ~0%, 60.5%, ~0%, and 39.5%, respectively.

EXAMPLE 7

The reaction was carried out in the same manner as described in Example 1 except that methallyl chloride was used in place of the allyl chloride and the reaction temperature was set at 40°C. The conversion yield of cyclopentene was 51.2%. The amounts of components (1), (2), (3) and (4) were ~0%, 52.4%, and 31.7%, respectively.

EXAMPLE 8

Toluene (70 ml) and cyclopentene (30 ml) were poured into a 200 ml two-necked flask under a stream of argon and then maintained at 30°C. Subsequently, allyl chloride (3.0 mmol). 1.0 ml of wolfram hexachloride solution (0.050 mmol/ml of toluene) and 0.65 ml of triethyl aluminum solution (0.92 mmol/ml of n-heptane) were added to the flask. The reaction was spontaneously and immediately initiated, and was continued for 1.5 hours. After the completion of the reaction, the catalysts were degraded by adding small amounts of methanol. The reaction mixture was distilled at ambient pressure to remove solvents and then was distilled under reduced pressure to yield the following components:

| | |
|---|---|
| (1) | small amounts |
| (2) | 58.5% |
| (3) | 33.2% |
| (4) | 8.3% |

Conversion yield of cyclopentene was 75.0%.

EXAMPLE 9

The reaction was conducted in the same manner as described in Example 8 except that the amount of triethyl aluminum solution was 0.27 ml. The conversion yield of cyclopentene was 50.0%. The amounts of components (1), (2), (3) and (4) were a small amount, 52.5%, 42.5% and 5.0%, respectively.

Cyclic polyenes thus obtained can be used as starting materials for polymers and intermediates for organic synthesis by taking advantages of special features of molecular structure of them. That is, large ring ketone, dicarboxylic acid and lactum can be obtained by oxidizing cyclic polyenes of the present invention. These substances are utilized as materials for producing perfume, additive for lubricating oil and polymer such as nylon. Also, the cyclic polymers are used to make polymers which are elastmers and are utilized as rubber materials. The elastmers can be obtained by working such radical initiator as sulfur, peroxide and the like substances on the cyclic polyenes, preferably in the presence of styrene or divinylbenzene in order to crosslinking them.

Lactam is obtained by acting hydroxylamine on large ring ketone which is prepared by oxidizing 10 or 15 cyclic polyenes. Further, nylon 10 (density: 1.08, melting point: 190° to 200°C) and nylon 15 (density: 1.01, melting point: 178° to 180°C) are produced by condensing the lactam with alkaline.

Large ring polyenes are obtained by ring-opening polymerization, which is done by working such metathesis catalyst as $WCl_6$-$C_2H_5AlCl_2$ catalyst on the cyclic polyenes.

I claim:

1. A polymerization process for producing cyclic polyenes having the general formula

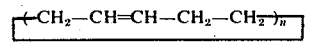

wherein $n$ is from 2 to 4, comprising polymerizing cyclopentene by contacting it with a catalyst consisting essentially of a composition of (i) trialkyl aluminum containing as the alkyl group a $C_1$-$C_6$ alkyl group, (ii) tungsten hexahalide; and (iii) allyl halide or methallyl halide at a temperature between about −20° to 100°C; in the said catalyst, the molar ratio of trialkyl aluminum to tungsten hexahalide is between about 4:1 and 15:1, the molar ratio of allyl halide or methallyl halide to tungsten hexahalide is between about 40:1 and 120:1, and the amount of tungsten hexahalide is from 0.0001 to 0.1 moles per 1 mole of cyclopentene.

2. The process according to claim 1 for producing polyenes having the general formula

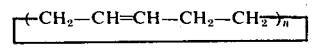

wherein $n$ is at least 2, and wherein the molar ratio of trialkyl aluminum to wolfram hexahalide is between about 4:1 and 15:1, the molar ratio of allyl halide or methallyl halide to wolfram hexahalide is between about 40:1 and 120:1, and the amount of wolfram hexahalide is from 0.0001 to 0.1 moles per 1 mole of cyclopentene.

3. The process according to claim 1, wherein the polymerization reaction is carried out in the presence of an aromatic hydrocarbon solvent.

4. The process according to claim 3, wherein said aromatic hydrocarbon is a member selected from the group consisting of benzene, toluene, and xylene.

5. The process according to claim 1, wherein the polymerization reaction is carried out at a temperature of between about 0° and 60°C.

6. The process according to claim 5, wherein the polymerization reaction is carried out in the presence of a solvent selected from the group consisting of benzene, toluene, and xylene, and wherein said halides are selected from the group consisting of chlorides and bromides.

7. The process according to claim 6, wherein said trialkyl aluminum is triethyl aluminum.

8. 9. The process according to claim 6, wherein said trialkyl aluminum is tri-iso-butyl aluminum.

* * * * *